(12) United States Patent
McHugo

(10) Patent No.: US 9,358,095 B2
(45) Date of Patent: Jun. 7, 2016

(54) ANTI-REFLUX PROSTHESIS

(71) Applicant: Cook Medical Technologies LLC, Bloomington, IN (US)

(72) Inventor: Vincent McHugo, Birdhill (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/060,338

(22) Filed: Oct. 22, 2013

(65) Prior Publication Data

US 2014/0114433 A1 Apr. 24, 2014

Related U.S. Application Data

(60) Provisional application No. 61/718,078, filed on Oct. 24, 2012.

(51) Int. Cl.
*A61F 2/04* (2013.01)
*A61F 2/24* (2006.01)

(52) U.S. Cl.
CPC ............... *A61F 2/04* (2013.01); *A61F 2/2412* (2013.01); *A61F 2002/044* (2013.01); *A61F 2002/045* (2013.01)

(58) Field of Classification Search
CPC  A61F 2002/044; A61F 2/2475; A61F 2/2412
USPC ................. 623/23.64, 23.65, 23.68
See application file for complete search history.

(56) References Cited

U.S. PATENT DOCUMENTS

| 4,434,810 | A | 3/1984 | Atkinson |
| 4,846,836 | A | 7/1989 | Reich |
| 5,314,473 | A | 5/1994 | Godin |
| 5,392,775 | A | 2/1995 | Adkins, Jr. et al. |
| 5,861,036 | A | 1/1999 | Godin |
| 6,264,700 | B1 * | 7/2001 | Kilcoyne ............ A61F 2/04 623/23.68 |

(Continued)

FOREIGN PATENT DOCUMENTS

| EP | 1 430 853 B1 | 6/2004 |
| EP | 1 704 834 B1 | 9/2006 |

(Continued)

OTHER PUBLICATIONS

International Search Report and Written Opinion of the International Searching Authority for International Application No. PCT/US2013/064780, dated Jan. 3, 2014, 9 pages.

*Primary Examiner* — Thomas J Sweet
*Assistant Examiner* — Daniel Bissing
(74) *Attorney, Agent, or Firm* — Brinks Gilson & Lione

(57) ABSTRACT

A prosthesis and a method for controlling flow through a bodily lumen in a first direction and a second direction are provided. The prosthesis includes a body having a proximal portion, a distal portion and a body lumen extending therethrough. The prosthesis also includes a first valve for controlling flow through the body lumen in a first direction where the first valve forms a first opening in the prosthesis. The prosthesis includes a second valve for controlling flow through the body lumen in a second direction where the second valve includes a portion that contacts the body in a closed configuration and the portion is spaced apart from the body in an open configuration to form the second opening. The first opening is positioned apart from the second opening and the second opening opens in response to a higher pressure than the first opening.

20 Claims, 6 Drawing Sheets

(56) References Cited

U.S. PATENT DOCUMENTS

| | | |
|---|---|---|
| 6,302,917 B1 | 10/2001 | Dua et al. |
| 6,544,291 B2 | 4/2003 | Taylor |
| 6,746,489 B2 | 6/2004 | Dua |
| 6,790,237 B2 | 9/2004 | Stinson |
| 7,118,600 B2 | 10/2006 | Dua et al. |
| 7,182,788 B2 | 2/2007 | Jung et al. |
| 7,354,455 B2 | 4/2008 | Stinson |
| 7,993,410 B2 | 8/2011 | Shin et al. |
| 8,029,557 B2 | 10/2011 | Sobrino-Serrano et al. |
| 8,221,505 B2 | 7/2012 | Skerven |
| 2003/0040808 A1 | 2/2003 | Stack et al. |
| 2004/0102855 A1 | 5/2004 | Shank |
| 2005/0137681 A1 | 6/2005 | Shoemaker et al. |
| 2007/0213813 A1 | 9/2007 | Von Segesser et al. |
| 2008/0086214 A1 | 4/2008 | Hardin et al. |
| 2009/0138071 A1 | 5/2009 | Cheng et al. |
| 2009/0171447 A1 | 7/2009 | Von Segesser et al. |
| 2010/0036504 A1 | 2/2010 | Sobrino-Serrano et al. |
| 2010/0114327 A1 | 5/2010 | Sobrino-Serrano |
| 2010/0121461 A1 | 5/2010 | Sobrino-Serrano et al. |
| 2010/0121462 A1 | 5/2010 | Sobrino-Serrano et al. |
| 2010/0137998 A1 | 6/2010 | Sobrino-Serrano et al. |
| 2011/0160836 A1 | 6/2011 | Behan |
| 2011/0190905 A1 | 8/2011 | Behan |
| 2012/0059486 A1 | 3/2012 | Sobrino-Serrano et al. |
| 2012/0089236 A1 | 4/2012 | Errico et al. |
| 2012/0158026 A1 | 6/2012 | Behan |
| 2012/0197386 A1 | 8/2012 | Von Segesser et al. |

FOREIGN PATENT DOCUMENTS

| | | |
|---|---|---|
| EP | 1 952 785 B1 | 8/2008 |
| EP | 2 248 486 A2 | 11/2010 |
| EP | 2 316 381 A2 | 5/2011 |
| EP | 2 368 527 A1 | 9/2011 |
| EP | 2 387 973 A1 | 11/2011 |
| GB | 1 354 691 A | 5/1974 |
| WO | WO 01/66190 A2 | 9/2001 |
| WO | WO 03/030782 A1 | 4/2003 |
| WO | WO 2005/011534 A1 | 2/2005 |
| WO | WO 2006/004679 A1 | 1/2006 |
| WO | WO 2008/028569 A1 | 3/2008 |
| WO | WO 2011/073970 A1 | 6/2011 |
| WO | WO 2013/144770 A2 | 10/2013 |
| WO | WO 2014/022500 A1 | 2/2014 |

\* cited by examiner

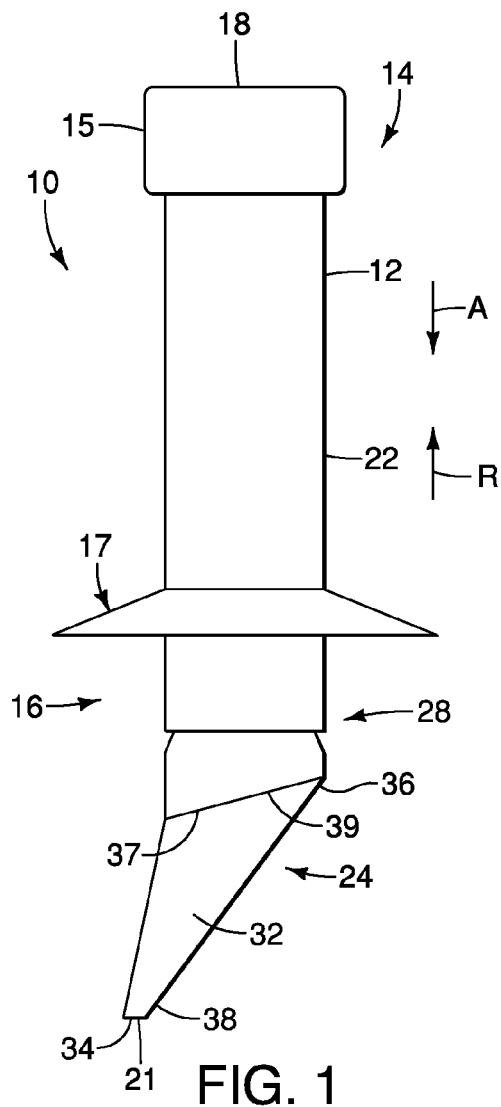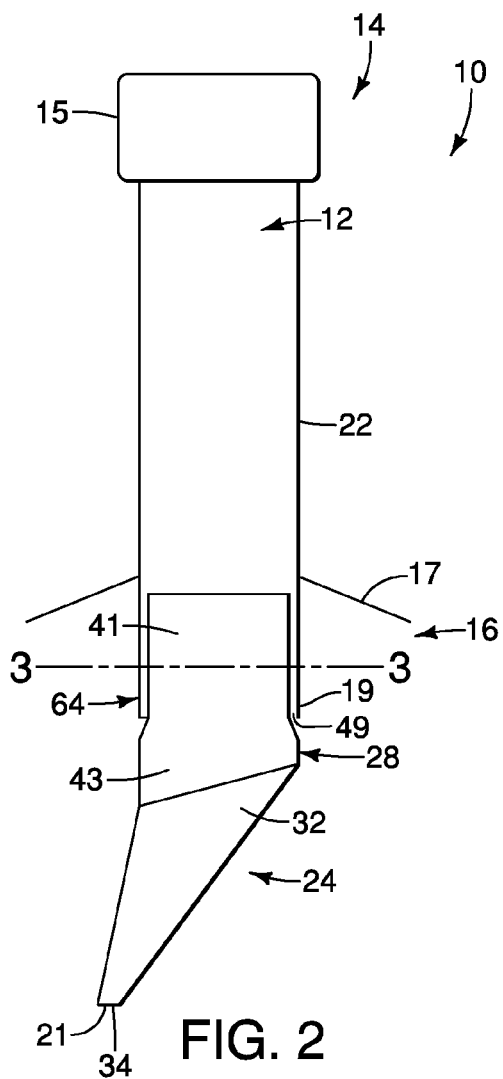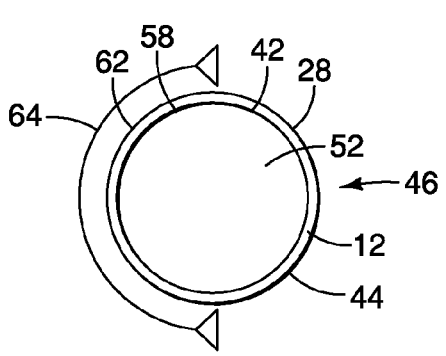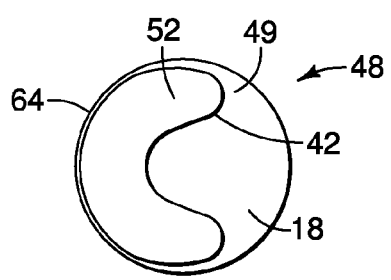

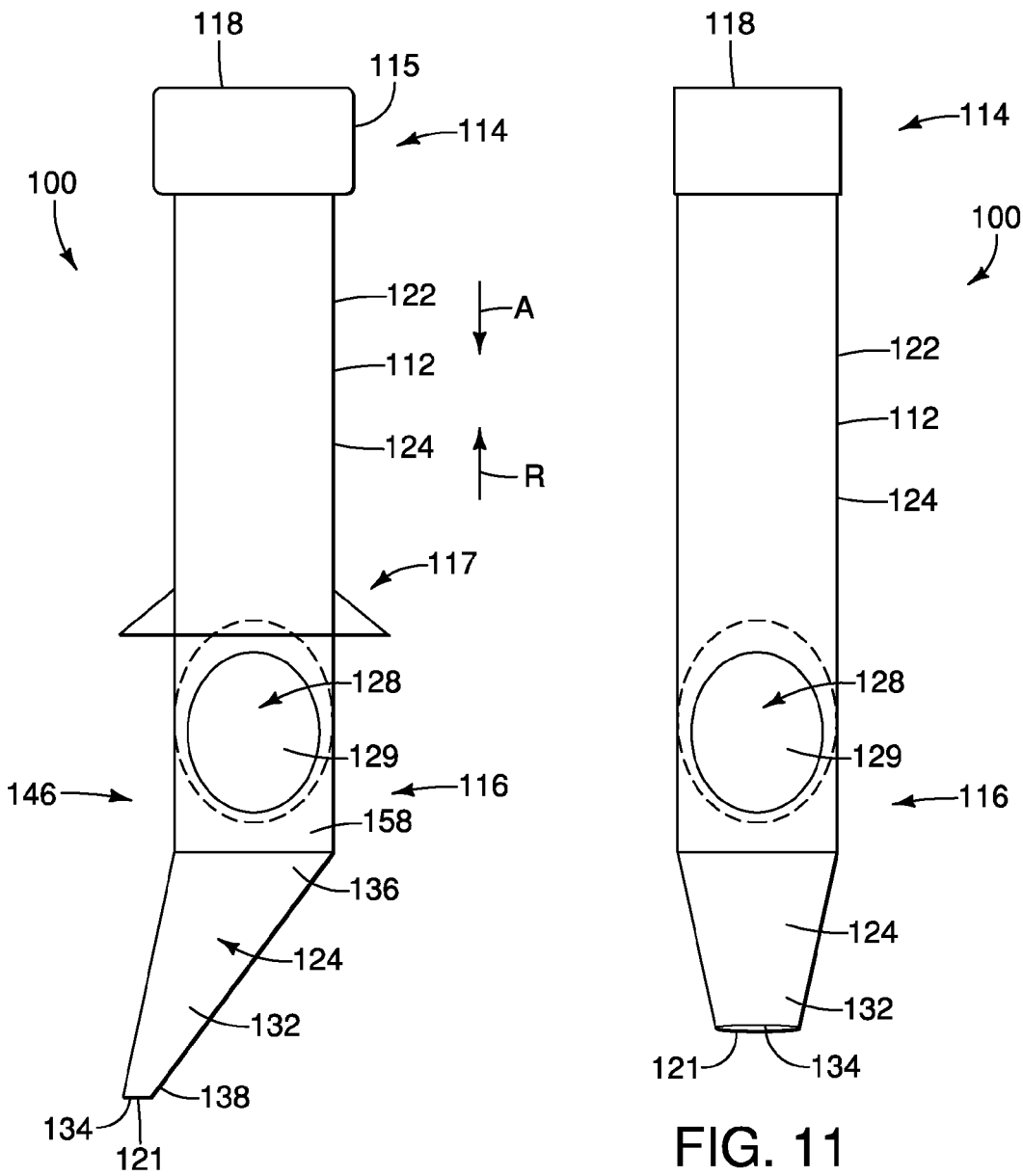
FIG. 10A
FIG. 11
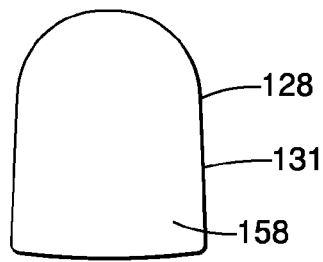
FIG. 10B

ANTI-REFLUX PROSTHESIS

CROSS-REFERENCE TO RELATED APPLICATIONS

This application claims the benefit of U.S. Provisional Application No. 61/718,078, filed Oct. 24, 2012, which is incorporated herein by reference in its entirety.

FIELD OF THE INVENTION

The present invention relates to medical devices and in particular to a prosthesis for regulating fluid flow through a lumen.

BACKGROUND OF THE INVENTION

The lower esophageal sphincter (LES) in healthy individuals allows food to pass into the stomach, but prevents gastric fluids from moving into the esophagus except when the patient vomits. Aspiration is a clinical risk for patients having a malfunctioning LES or for patients having stents placed across the gastroesophageal junction (GEJ) so that an opening is created at the bottom of the esophagus that can lead to acid reflux and aspiration. Aspiration occurs when the stomach contents travel from the stomach into the lungs. Aspiration in the lungs can lead to pneumonia or death. Risk of aspiration in patients having a compromised LES increases when the patient is in a prone position.

Anti-reflux esophageal prostheses or stents have been developed to treat tumors or strictures in the vicinity of the LES. An anti-reflux esophageal prosthesis or stent is typically placed in the lower esophagus and through the LES to maintain the patency thereof due to the presence of a cancerous tumor commonly found in the vicinity thereof or to treat benign tumor conditions, such as blockage or strictures.

A problem with an esophageal prosthesis or stent is that fluid from the stomach flows into the mouth of the patient when in a prone position, increasing the risk of aspiration. In an attempt to solve the problem, a number of esophageal prostheses or stents utilize a one-way valve such as a duck-bill or reed-type valve in which only food or fluid from the esophagus flows into the stomach in only an antegrade or forward direction. However, these one-way anti-reflux prostheses or stents present another problem. When the patient wants to belch or vomit, the patient is prevented from doing so, because the one-way valve prevents backward flow in the retrograde direction. Such condition is not only painful to the patient, but can also lead to more complicated medical conditions. Some esophageal prostheses or stents use a sleeve that extends into the stomach to control the flow of fluids. However, at standard pressure within the stomach, and in the absence of external pressure (i.e. standard temperature and pressure) such as when the patient is in the prone position, the sleeve may not seal to prevent reflux of the stomach contents into the mouth.

What is needed is a prosthesis that is normally closed to prevent gastric fluids from entering the esophagus even in the absence of external pressure within the stomach (i.e. at standard temperature and pressure), allows food to pass into the stomach and also allows for vomiting and belching when necessary and returns to the closed position.

BRIEF SUMMARY

Accordingly, it is an object of the present invention to provide a device and a method having features that resolve or improve on the above-described drawbacks.

A prosthesis for controlling flow through a bodily lumen in a first direction and a second direction is provided. The prosthesis includes a body having a proximal portion, a distal portion and a body lumen extending therethrough. The prosthesis also includes a first valve for controlling flow through the body lumen in a first direction where the first valve forms a first opening in the prosthesis. The prosthesis includes a second valve for controlling flow through the body lumen in a second direction where the second valve includes a portion that contacts the body in a closed configuration and the portion is spaced apart from the body in an open configuration to form the second opening. The first opening is positioned apart from the second opening and the second opening opens in response to a higher pressure than the first opening.

In another aspect, a method for controlling flow through a bodily lumen in a first direction and a second direction is provided. The method includes positioning a body of a prosthesis within the bodily lumen. The prosthesis includes a first valve and a second valve, the first valve controls flow through the body lumen in a first direction and the first valve forms a first opening in the prosthesis. The second valve controls flow through the body lumen in a second direction and the second valve includes a portion that contacts the body in a closed configuration and the portion is spaced apart from the body in an open configuration to form the second opening. The method further includes opening the first valve in response to the flow in the first direction; and opening the second valve in response to the flow in the second direction where a pressure required to open the second valve is greater than a pressure required to open the first valve. The first valve is closed in the absence of the flow in the first direction and the second valve is closed in the absence of flow in the second direction at the higher pressure.

BRIEF DESCRIPTION OF THE DRAWINGS

FIG. 1 is a side view of a prosthesis in accordance with an embodiment of the present invention;

FIG. 2 is a sectional view of the embodiment shown in FIG. 1;

FIG. 3 is a cross sectional view across the line 3-3 shown in FIG. 2 with a second valve in an closed configuration;

FIG. 4 is a cross sectional view across the line 3-3 shown in FIG. 2 with a second valve in an open configuration;

FIG. 10A is a is a side view of a prosthesis in accordance with an embodiment of the present invention;

FIG. 10B is a side view of a second valve in accordance with an embodiment of the present invention;

FIG. 11 is a is a side view of a prosthesis in accordance with an embodiment of the present invention;

DETAILED DESCRIPTION

Figure 5:
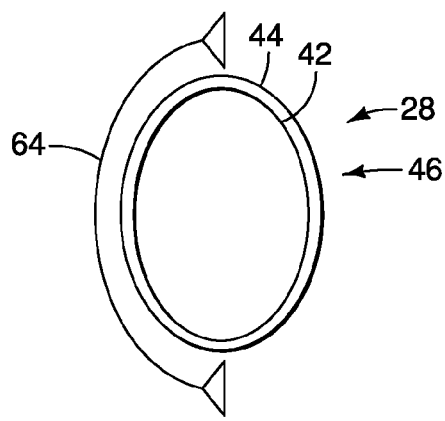
FIG. 5 is a cross-sectional view of a prosthesis in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the prosthesis to a patient. Hence the term "distal" means the portion of the prosthesis that is farthest from the physician and the term "proximal" means the portion of the prosthesis that is nearest to the physician.

The present invention relates to medical devices, and in particular to prosthetic devices for implantation in a body lumen such as the lower esophageal sphincter or a vessel. As used herein, the term "implantable" refers to an ability of a medical device to be positioned at a location within a body, such as within a body lumen, either temporarily, semi-permanently, or permanently. Permanent fixation of the device in a particular position is not required. Furthermore, the terms "implantation" and "implanted" refer to the positioning of a medical device at a location within a body, such as within a body lumen.

Figure 8:
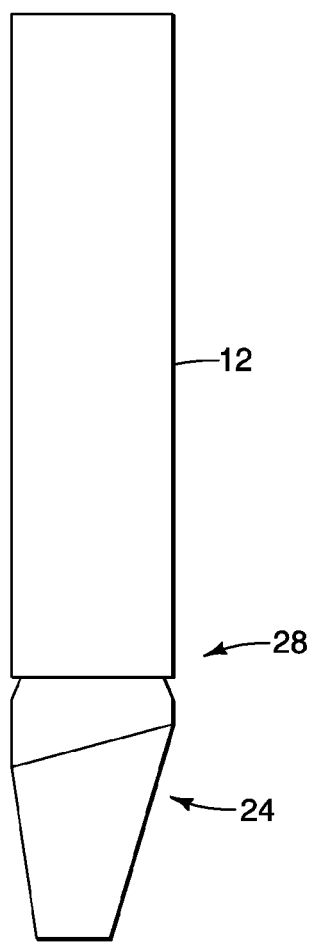
FIG. 8 is a side view of a prosthesis in accordance with an embodiment of the present invention.

FIG. 1 illustrates a prosthesis 10 in accordance with an embodiment of the present invention. The prosthesis 10 includes a body 12 having proximal portion 14, a distal portion 16 and a lumen 18 extending therethrough. In some embodiments, the body 12 may be an expandable stent such as a self-expandable stent or a balloon expandable stent. Non-limiting examples of expandable stents include the Z-Stent® and the EVOLUTION® stent (Cook Medical Incorporated, Bloomington, Ind.). In some embodiments, the body 12 may be a non-expandable tubular stent. In some embodiments, the proximal portion 14 of the body 12 may include an end portion 15 having an expanded outer diameter. In some embodiments, the distal portion 16 may include an end portion having an expanded outer diameter or an anti-migration collar 17 as shown in FIG. 1 to facilitate positioning of the body 12 at the delivery site. In some embodiments, the body 12 may be a substantially straight tubular shape as shown in FIG. 8. The body 12 may include a coating 22 that is liquid impermeable so that liquid and nutrients flowing from the proximal portion 14 to the distal portion 16 or stomach contents from the distal portion 16 to the proximal portion 14 do not pass through a wall 24 of the body 12.

Figure 14:
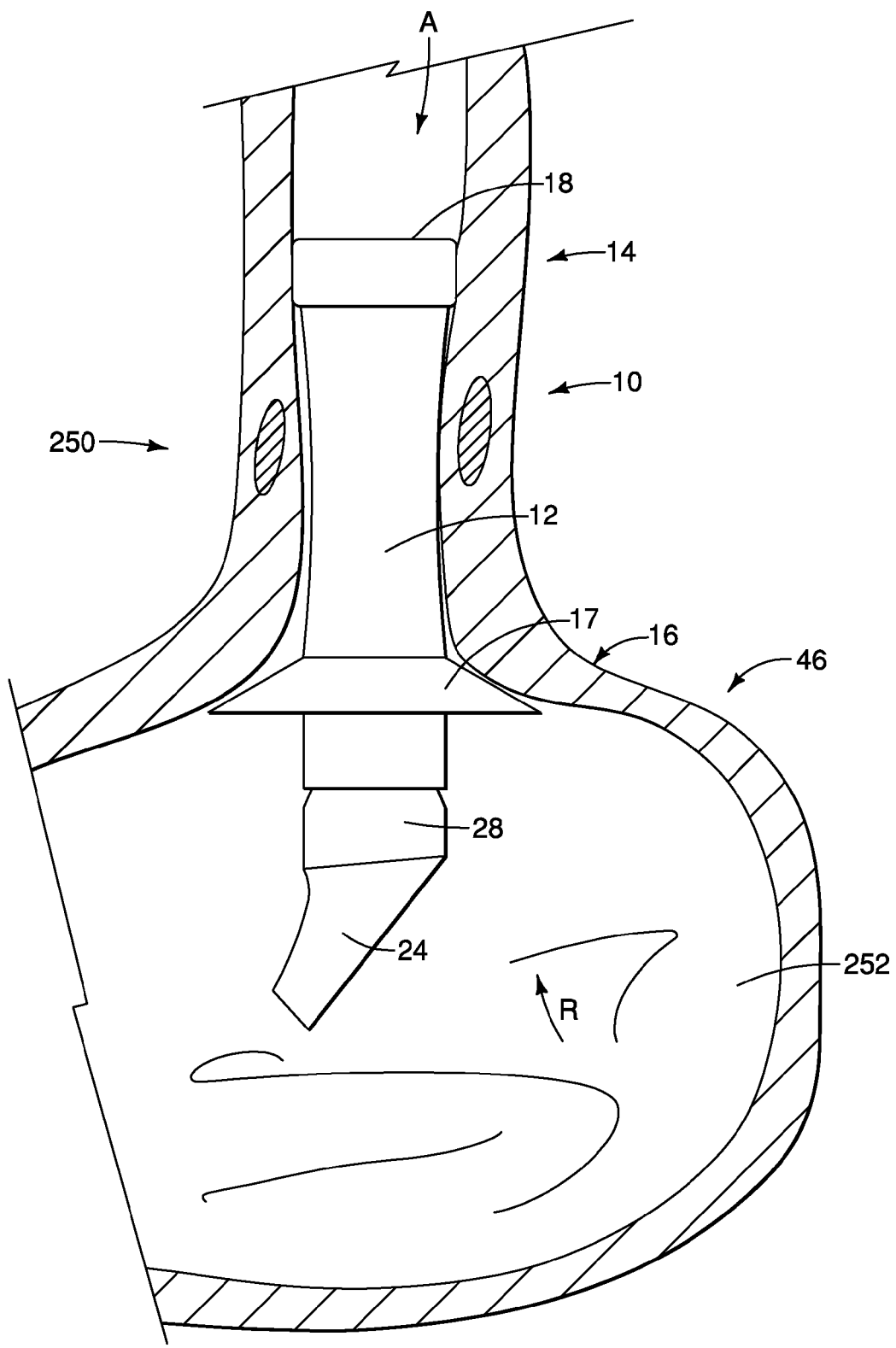
FIG. 14 illustrates an embodiment of a prosthesis positioned within the lower esophageal sphincter.

As shown in FIG. 1, the prosthesis 10 includes a first valve 24 and a second valve 28. Both the first valve 24 and the second valve 28 may be configured to be one-way valves. In the embodiment shown in FIG. 1, the first valve 24 is configured to be a low pressure valve and to allow antegrade flow through the lumen 18, for example from the patient's mouth to the stomach when the prosthesis 10 is positioned in the lower esophageal sphincter (LES) as shown in FIG. 14. The second valve 28 is configured to be a high pressure valve and to allow retrograde flow through the lumen 18, for example from the patient's stomach to the mouth. Generally, the retrograde flow is at a higher pressure than the antegrade flow. The retrograde flow may be the result of the patient burping or vomiting and the antegrade flow may be the result of the patient swallowing liquids or food that then flows into the lumen 18 to the body 12 to the first valve 24.

In some embodiments, the first valve 24 may be connected to the second valve 28. In some embodiments, the first valve 24 may be connected to the body 12. In some embodiments, the first valve 24 may be provided as a flexible sleeve 32 having a lumen 34 extending therethrough and operably connected to the lumen 18 of the body 12. The first valve 24 is configured to be opened so that a first valve opening 21 is formed in the presence of antegrade flow and closable on itself in the absence of flow in the antegrade direction. The first valve 24 is configured so that retrograde flow cannot flow through the first valve 24 and stomach contents cannot leak back through the valve 24 even when the patient is in a prone position or when the stomach contents are at about atmospheric pressure. The prosthesis 10 is configured so that retrograde flow flows through the second valve 28 as described below. In some embodiments, the first valve 24 may be sized and shaped or include one or more modifications so that the first valve 24 cannot evert into the body 12 and allow retrograde flow through the lumen 34 of the first valve 24. As shown in FIG. 1, the first valve 24 may include a modification so that the first valve 24 is tapered from a proximal portion 36 to a distal portion 38 of the first valve 24. An angle of the taper may be greater on one portion of the first valve 24 relative to the remainder of the first valve 24 to facilitate one way flow through the first valve 24. By way of non-limiting example, the first valve 24 may include modification such as a narrowed distal portion 38 relative to the proximal portion 36, a wider distal portion 38 relative to the proximal portion 36, a thickened distal portion 38 relative to the proximal portion 34, a thickened proximal portion 36 relative to the distal portion 38 or other modifications to prevent retrograde flow through the first valve 24 and to prevent the first valve 24 from everting. As shown in FIG. 8, the first valve 24 may extend distally without including a taper. The first valve 24 shown in FIG. 8 may include one or more of the modifications described above to prevent the first valve from everting in the presence of retrograde pressure.

Figure 9:
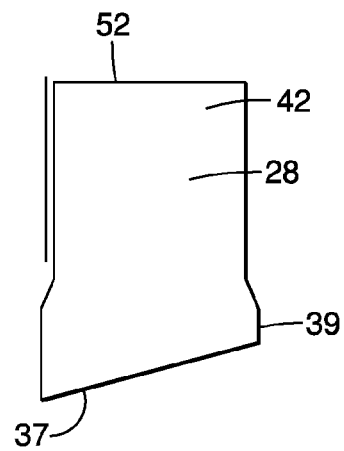
FIG. 9 is a side view of a second valve in accordance with an embodiment of the present invention.

FIGS. 1 and 2 illustrate an embodiment of the second valve 28 of the prosthesis 10. As shown in FIGS. 1 and 2, the second valve 28 may be positioned about the distal portion 16 of the body 12. FIG. 2 illustrates that a proximal portion 41 of the second valve 28 may be partially positioned within the lumen 18 at the distal portion 16 of the body 12. A distal portion 43 of the second valve may extend distal to the distal portion 16 of the body 12. The proximal portion 41 of the second valve 28 may be sized and shaped to complement the size and shape of the distal portion 16 of the body 12. A cross sectional view through the body 12 and the second valve 28 is shown in FIG. 3 with the second valve 28 in a closed configuration 46. The second valve 28 is shown in an open configuration 48 in FIG. 4. In some embodiments, the second valve 28 may include an angled portion 37 at a distal end 39 of the second valve 28. The second valve 28 may also include an expanded outer diameter at the distal end 38 that may extend distal to a distal end 19 of the body 12. An embodiment of the second valve 28 is shown in FIG. 9.

Figure 6:
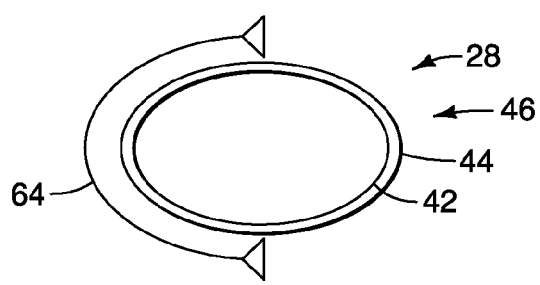
FIG. 6 is a cross-sectional view of a prosthesis in accordance with an embodiment of the present invention.
Figure 7:
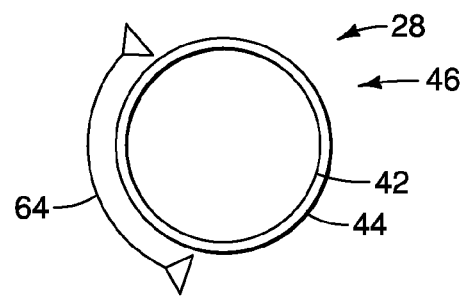
FIG. 7 is a cross-sectional view of a prosthesis in accordance with an embodiment of the present invention.

As shown in FIG. 3, an outer wall 42 of the second valve 28 is sized and shaped to fit against an inner wall 44 of the body 12. The lumen 18 of the body 12 connects to a lumen 52 of the second valve 28. In some embodiments, the lumen 52 of the second valve 28 connects to the lumen 34 of the first valve 24. A portion 58 of the outer wall 42 is connected to a portion 62 of the inner wall 44 of the body 12 forming a connected region 64 of the prosthesis 10. The connected region 64 is indicated as the region between the arrows shown in FIG. 3. The connection may be formed by any method known to one skilled in the art. By way of non-limiting example, the portion 58 of the outer wall 42 may be connected to the portion 62 of the body 12 by bonding, welding, gluing and the like. In some embodiments, at least portions of the body 12 and the second valve 28 may be woven and the woven material is covered by a silicone sleeve. The portions of the silicone sleeves on the outer wall 42 and the inner wall 44 may bonded together with a silicone elastomer. In some embodiments, the connected region 64 of the prosthesis 10 may be about 180° of the circumference of the body 12 with the remainder of the outer wall 42 and the inner wall 44 unconnected (See for example, FIGS. 3, 5 and 6). In some embodiments, the connected region may be more or less than about 180° of the circumference of the body 12. (See for example, FIG. 7.) FIGS. 5 and 6 also illustrate alternative shapes for the distal portion 16 of the body 12. The shape and the size of the connected region can be used to modify the force in the retrograde direction needed to open the second valve 28. The cross-sectional shape of the second valve may be circular, oval, curvilinear or any shape suitable to respond to a pressure change to open the second valve 28 in response to a sufficient increase in pressure external to the second valve 28. The material used to form the valve 28 and the body 12 and if woven, the type of weave and pitch of the weave, may also be used to control the amount of pressure needed to open the second valve 28. By way of non-limiting example, the body 12 may have a higher radial force than the valve 28. In some embodiments, the diameter and the pitch of the wire used to form the woven body 12 and with woven valve 28 may be varied to change the pressure at which the valve 28 opens and closes. In some embodiments, the valve 28 may have a larger diameter than the body 12 and may be compressed to position a portion of the valve 28 within the body 12 to create a continuous pressure to keep the valve 28 closed until the pressure against second valve 28 is sufficiently elevated to open the valve 28.

As shown in FIG. 4, the second valve 28 is in the open configuration 48 with the wall 42 of the second valve 28 spaced apart from the wall 44 of the body 12 so that the lumen 18 of the body 12 is exposed and a second valve opening 49 is formed in the prosthesis 10. Retrograde flow, for example from the stomach to the mouth, can enter the lumen 18 through the opening 49 when the second valve 28 is in the open configuration 48 and flow toward the proximal portion 14 of the body 12. The connected portion 64 remains connected and the wall 42 moves away from the wall 44 to the open configuration 46 when the pressure of the retrograde flow becomes sufficiently high.

An alternative embodiment of a prosthesis 100 is shown in FIGS. 10-13. Portions of the prosthesis 100 are similar to the prosthesis 10 described above and features of the prosthesis 10 may be included on the prosthesis 100. As shown in FIG. 10A, the prosthesis 100 includes a body 112 having a proximal portion 114, a distal portion 116 and a lumen 118 extending therethrough. In some embodiments, the body 112 may be an expandable stent such as a self-expandable stent or a balloon expandable stent. Non-limiting examples of expandable stents include the Z-Stent® and the EVOLUTION® stent (Cook Medical Incorporated, Bloomington, Ind.). In some embodiments, the body 112 may be a non-expandable tubular stent. In some embodiments, the proximal portion 114 of the body 112 may include an end portion 115 having an expanded outer diameter. In some embodiments, the distal portion 116 may include an end portion having an expanded outer diameter or an anti-migration collar 117 as shown in FIG. 10A to facilitate positioning of the body 112 at the delivery site. In some embodiments, the body 112 may be a substantially straight tubular shape as shown in FIG. 11. The body 112 may include a coating or sleeve 122 that is liquid impermeable so that liquid and nutrients flowing from the proximal portion 114 to the distal portion 116 or stomach contents flowing from the distal portion 116 to the proximal portion 114 do not pass through a wall 124 of the body 112.

As shown in FIGS. 10A and 11, the prosthesis 100 includes a first valve 124 and a second valve 128. Both the first valve 124 and the second valve 128 may be configured to be one-way valves. In the embodiment shown in FIGS. 10A and 11, the first valve 124 is configured to be a low pressure valve and to allow antegrade flow through the lumen 118, for example from the patient's mouth to the stomach when the prosthesis 100 is positioned in the lower esophageal sphincter LES (See for example, FIG. 14, showing the position of a prosthesis in the LES). The first valve 124 is configured to be opened so that a first valve opening 121 is formed in the presence of antegrade flow and closable on itself in the absence of flow in the antegrade direction. The second valve 128 is configured to be a high pressure valve and to allow retrograde flow through the lumen 118 of the body 112, for example from the patient's stomach to the mouth. As discussed above, the retrograde flow is at a higher pressure than the antegrade flow. The retrograde flow may be the result of the patient burping or vomiting and the antegrade flow may be the result of the patient swallowing liquids or food that then flows into the lumen 118 to the body 112 and through the first valve 124.

In some embodiments, the first valve 124 may be connected to the second valve 128. In some embodiments, the first valve 124 may be connected to the body 112 as shown in FIGS. 10A and 11. In some embodiments, the first valve 124 may be provided as a flexible sleeve 132 having a lumen 134 extending therethrough and operably connected to the lumen 118 of the body 112. The first valve 124 is configured to be closable on itself in the absence of flow in the antegrade direction. The first valve 124 is configured so that retrograde flow cannot flow through the first valve 124 and stomach contents cannot leak back through the first valve 124 even when the patient is in a prone position or when the stomach contents are at about atmospheric pressure. The prosthesis 100 is configured so that retrograde flow flows through the second valve 128 as described below. In some embodiments, the first valve 124 may be sized and shaped or include one or more modifications so that the first valve 124 cannot evert into the body 112 and allow retrograde flow through the lumen 134 of the first valve 124. As shown in FIG. 10A, the first valve 124 may include a modification so that the first valve 124 is tapered from a proximal portion 136 to a distal portion 138 of the first valve 124. An angle of the taper may be greater on one portion of the first valve 124 relative to the remainder of the first valve 124 to facilitate one way flow through the first valve 124. By way of non-limiting example, the first valve 124 may include modification such as a narrowed distal portion 138 relative to the proximal portion 136, a wider distal portion 138 relative to the proximal portion 136, a thickened distal portion 138 relative to the proximal portion 134, a thickened proximal portion 136 relative to the distal portion 138 or other modifications to prevent retrograde flow through the first valve 124 and to prevent the first valve 124 from everting. As shown in FIG. 11, the first valve 124 may extend distally without including a taper. The first valve 124 shown in FIG. 11 may include one or more of the modifications described above to prevent the first valve 124 from everting in the presence of retrograde pressure.

Figure 12A:
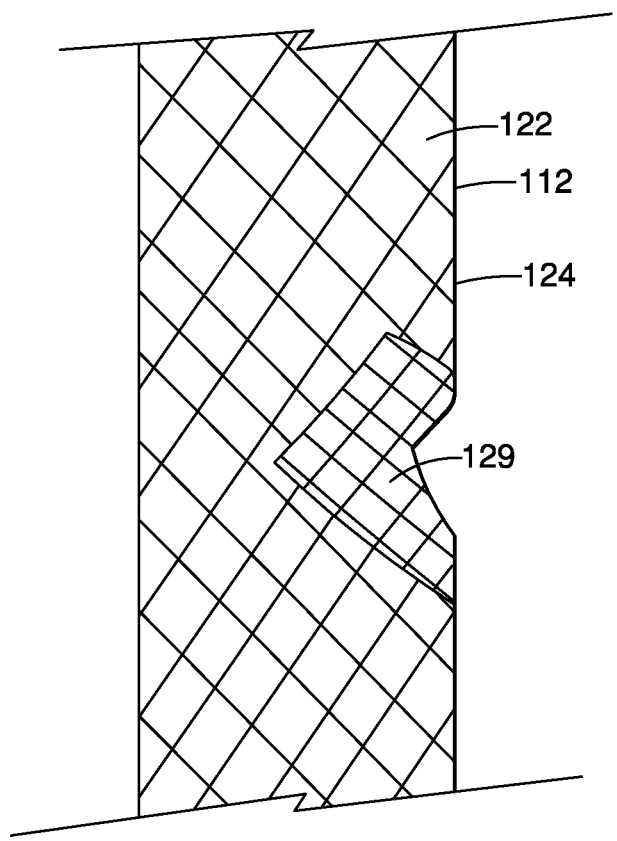
FIG. 12A is a partial side view of a body of an embodiment of the prosthesis in accordance with the present invention.
Figure 12B:
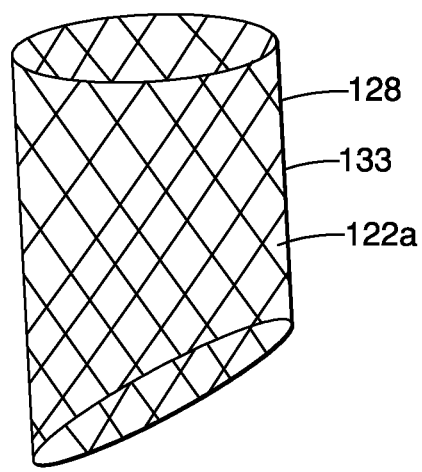
FIG. 12B is a perspective view of a second valve in accordance with an embodiment of the present invention.

An embodiment of the second valve 128 of the prosthesis 100 is shown in FIG. 10A. The second valve 128 may be positioned within the body 112 to cover an opening 129 formed in the wall 124 of the body 112. The opening 129 in the wall 124 is shown in FIG. 12A with the valve 128 removed for clarity. The valve 128 may be provided as flap portion 131 that is sized and shaped to movably cover the opening 129. The flap portion 131 is shown in FIG. 10B. The flap portion 131 may be woven or nonwoven and may be curved to fit inside the curved interior of the body 112. In some embodiments, the valve 128 may be provided as a tubular body 133 as shown in FIG. 12B that is sized and shaped to fit within the body 112 to cover the opening 129. In some embodiments, the tubular body 133 may be woven and include a covering 122a so that fluid does not flow through the woven portion of the valve 128. As shown in FIG. 10A the second valve 128 is in a closed configuration 146 so that fluid from the stomach cannot enter the valve 128 until the pressure is increased enough to open the valve 128. The second valve 128 is shown in an open configuration 148 in FIG. 13 where the opening 129 is open and fluid and stomach contents can enter the lumen 118 of the body 112 through the opening 129.

A portion 158 of the valve 128 may be secured to the body 112. The connection of the portion 158 to the body 112 may be formed by any method known to one skilled in the art. By way of non-limiting example, the portion 158 may be connected to t the body 112 by bonding, welding, gluing and the like. In some embodiments, at least portions of the body 112 and the second valve 28 may be woven and the woven material is covered by a silicone sleeve. The portion 158 of the silicone valve 128 and the silicone covering 122 on the body 112 may bonded together with a silicone elastomer. The shape and the size of the connected region can be used to modify the force in the retrograde direction needed to open the second valve 128. The cross-sectional shape of the second valve 128 and/or the body 112 may be circular, oval, curvilinear or any shape suitable to respond to a pressure change to open the second valve 128 in response to a sufficient increase in pressure external to the second valve 128. The material used to form the valve 128 and the body 112 and if woven, the type of weave and pitch of the weave, may also be used to control the amount of pressure needed to open the second valve 128. By way of non-limiting example, the body 112 may have a higher radial force than the valve 128. In some embodiments, the diameter and the pitch of the wire used to form the woven body 112 and with woven valve 128 may be varied to change the pressure at which the valve 128 opens and closes. In some embodiments, the tubular body 133 may have a larger diameter than the body 112 and may be compressed to position the body 133 within the body 112 to create a continuous pressure to keep the valve 128 closed until the pressure against the body 133 is sufficiently elevated to open the valve 128.

Figure 13:
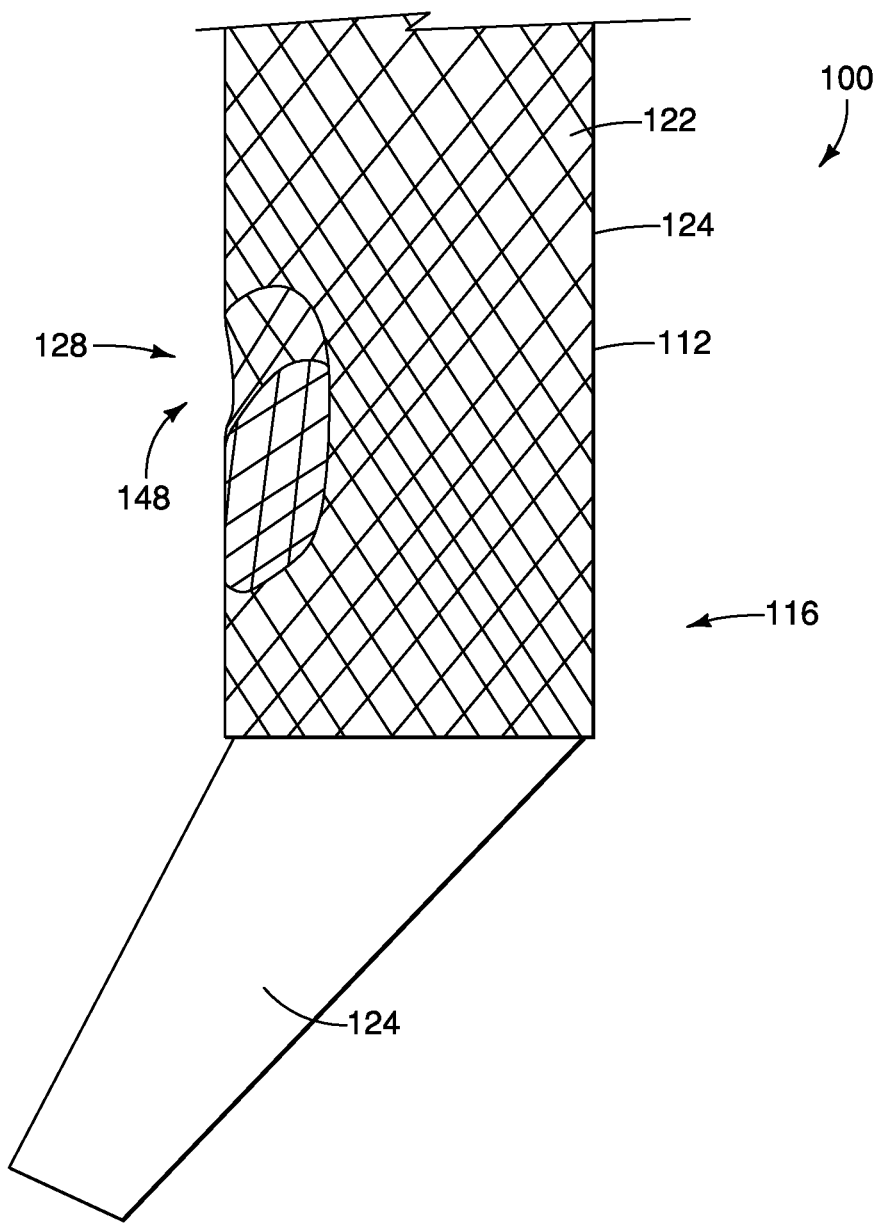
FIG. 13 is a partial perspective view of an embodiment with a second valve in an open configuration.

As shown in FIG. 13, the valve 128 is in the open configuration 148 with the second valve 128 spaced apart from the body 112 so that the opening 129 and the lumen 118 of the body 112 is exposed. Retrograde flow, for example from the stomach to the mouth, can enter the lumen 118 when the second valve 128 is in the open configuration 148 and flow toward the proximal portion 114 of the body 112. The prosthesis 100 returns to the closed configuration 146 when the pressure is reduced below the opening force.

The materials used to manufacture the components of the prosthetic devices described herein may be any materials known to one skilled in the art that are suitable for use in patients. By way of non-limiting example, the body may be formed from metals or polymers. Suitable exemplary metals include stainless steel and nitinol and the body may be woven or provided in a zig-zag configuration. Valves of the prosthetic devices of the embodiments may be made from any suitable biocompatible material that is liquid impermeable and that does not degrade in the presence of fluids or gastric material that comes in contact therewith. By way of non-limiting example, the first valve may be made from a medical grade polyurethane material, silicone, nylon, polyamides such as other urethanes, polyethylene, polyethylene terephthalate (PET), polystyrene-ethylene (PSE), polytetrafluoroethylene (PTFE), ultrahigh molecular weight, low density and high density polyethylene, elastomeric polyethylene, polyethyleneoxide (PEO), block copolymers containing polystyrene and poly(1,4-butadiene), ABA triblock copolymer made from poly(2-methyl-2-oxazoline), polytetrahydrofuran, shape memory polymers, amorphous or organic-inorganic hybrid polymers containing polymorbornere units or other biocompatible materials that are flexible and acid resistant. In some embodiments, portions of the valve may be made from biodegradable materials such as PLA, PLGA, PBA or nitinol. An exemplary material for the valve is a medical grade polyurethane material grade EG-80A material commercially known as TECOFLEX® polyurethane material (Thermedics, Incorporated, Woburn, Mass.). The first valve and the second valve of the embodiments described above may be made from the same or different materials. In some embodiments, the second valve may be formed from metals or polymers. Suitable exemplary metals include stainless steel and nitinol and the second valve may be woven. In some embodiments, portions of the prosthesis may be coated. An exemplary, non-limiting coating is a polymer such as silicone.

As shown in FIG. 14, the prosthesis 10 may be positioned in the lower esophageal sphincter 250. The prosthesis 100 may be similarly positioned. The proximal portion 14 of the body 12 may be positioned proximal to the esophageal sphincter 250. The distal portion 16 of the body 12 may be positioned so that the distal portion 16 and the first and second valves 24 and 28 extend into the stomach 252. The valve 24 may extend any distance into the stomach 250 and remain closed in the absence of antegrade pressure. The second valve 28 is shown positioned proximal to the first valve 24 and is shown in the closed configuration 46. The second valve 28 opens when the retrograde pressure reaches a sufficient level to open the second valve 28 and the first valve remains closed in response to the retrograde pressure. Both the first and second valve 24, 28 remain closed in the absence of antegrade and retrograde pressures. The prostheses 10, 100 may be delivered to the position in the esophageal sphincter in a collapsed configuration using a delivery device known to one skilled in the art.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A prosthesis for controlling flow through a bodily lumen, the prosthesis comprising:
   a body having a proximal portion, a distal portion and a body lumen extending therethrough;
   a first valve for controlling flow through the body lumen in a first direction, the first valve forming a first opening in the prosthesis; and
   a second valve for controlling flow through the body lumen in a second direction, the second valve comprising a tubular member that at least partially coextends longitudinally and circumferentially with the body, an outer wall of the second valve being sized and shaped to fit against at least a portion of an inner wall of the body, the second valve having a portion that contacts the body in a closed configuration and the portion is spaced apart from the body in an open configuration to form a second opening;

wherein the first opening is positioned apart from the second opening; and the second opening opens in response to a higher pressure than the first opening.

2. The prosthesis of claim 1, wherein the first valve is connected to the second valve and the first opening is positioned distal to the second valve.

3. The prosthesis of claim 1, wherein the first valve is connected to the body and extends distally from the body.

4. The prosthesis of claim 1, wherein the second valve is positioned at least partially within the body.

5. The prosthesis of claim 1, wherein a portion of the second valve extends distal to the distal portion of the body.

6. The prosthesis of claim 1, wherein the second valve is positioned within the body and a distal end of the second valve is proximal to a distal end of the body.

7. The prosthesis of claim 1, wherein the first valve comprises an asymmetrically tapered portion.

8. The prosthesis of claim 1, wherein the body comprises a higher radial force than the second valve.

9. The prosthesis of claim 1, wherein a diameter of the tubular member is greater than a diameter of the body.

10. The prosthesis of claim 1, wherein the cross-section shape of the body at the second valve is circular or oval.

11. The prosthesis of claim 1, further comprising an anti-migration collar connected to the body and extending radially away from the body.

12. The prosthesis of claim 1, wherein the second valve is partially connected to the body at a connection portion that extends partially around the body.

13. The prosthesis of claim 12, wherein the connection portion is about 180° around the body or less.

14. A method of controlling flow through a bodily lumen in a first direction and a second direction, the method comprising:

positioning a body of a prosthesis within the bodily lumen, the prosthesis including a first valve and a second valve, the first valve for controlling flow through the body lumen in a first direction, the first valve forming a first opening in the prosthesis and the second valve for controlling flow through the body lumen in a second direction, the second valve comprising a tubular member that at least partially coextends longitudinally and circumferentially with the body, an outer wall of the second valve being sized and shaped to fit against at least a portion of an inner wall of the body, the second valve having a portion that contacts the body in a closed configuration and the portion is spaced apart from the body in an open configuration to form a second opening;

opening the first valve in response to the flow in the first direction; and opening the second valve in response to the flow in the second direction where a pressure required to open the second valve is greater than a pressure required to open the first valve, the first valve being closed in the absence of the flow in the first direction and the second valve being closed in the absence of flow in the second direction at the higher pressure.

15. The method of claim 14, comprising providing the body having a higher radial force than the second valve.

16. The method of claim 14, comprising providing the first valve with a structure to prevent the first valve from everting in response to the flow in the second direction at the higher pressure.

17. The method of claim 14, comprising positioning the second valve against an opening in the body to form a closed configuration for the second valve.

18. The prosthesis of claim 1, wherein the first valve comprises a sleeve valve.

19. The prosthesis of claim 1, wherein the second valve, the body or both the second valve and the body comprise a woven material.

20. The prosthesis of claim 18, wherein the second valve, the body or both the second valve and the body comprise a woven material.

* * * * *